United States Patent
Kämper et al.

(10) Patent No.: US 11,591,638 B2
(45) Date of Patent: Feb. 28, 2023

(54) PROCESS AND COMPOSITION FOR THE STABILIZATION OF CELL-FREE NUCLEIC ACIDS AND CELLS

(71) Applicant: SARSTEDT AG & CO. KG, Nümbrecht (DE)

(72) Inventors: Martin Kämper, Engelskirchen-Osberghausen (DE); Tim Kinitz, Solingen (DE)

(73) Assignee: Sarstedt AG & Co. KG, Nümbrecht (DE)

( * ) Notice: Subject to any disclaimer, the term of this patent is extended or adjusted under 35 U.S.C. 154(b) by 98 days.

(21) Appl. No.: 16/635,085

(22) PCT Filed: Jul. 30, 2018

(86) PCT No.: PCT/EP2018/070633
§ 371 (c)(1),
(2) Date: Jan. 29, 2020

(87) PCT Pub. No.: WO2019/025387
PCT Pub. Date: Feb. 7, 2019

(65) Prior Publication Data
US 2021/0310045 A1    Oct. 7, 2021

(30) Foreign Application Priority Data
Aug. 2, 2017 (EP) .................... 17184585

(51) Int. Cl.
*C12Q 1/68* (2018.01)
*C12Q 1/6806* (2018.01)

(52) U.S. Cl.
CPC ..... *C12Q 1/6806* (2013.01); *C12Q 2527/125* (2013.01)

(58) Field of Classification Search
CPC .................................................. C12Q 1/6806
See application file for complete search history.

(56) References Cited

U.S. PATENT DOCUMENTS

2005/0181353 A1* 8/2005 Rao ....................... A01N 1/0226
514/56
2010/0280134 A1* 11/2010 Renard ................... A61P 35/00
435/6.12
2011/0065108 A1* 3/2011 Sherman .............. C12Q 1/6806
435/6.15
2012/0196830 A1* 8/2012 Parsons ................ A61K 31/728
514/56
2013/0137586 A1* 5/2013 Erbacher ................ A01N 1/021
435/6.12

FOREIGN PATENT DOCUMENTS

| WO | 2002/056030 A2 | 7/2002 |
|---|---|---|
| WO | 2003/018757 A2 | 3/2003 |
| WO | 2003/095974 A2 | 11/2003 |
| WO | 2004/017895 A2 | 3/2004 |
| WO | 2007/073397 A1 | 6/2007 |
| WO | 2013/045458 A1 | 4/2013 |
| WO | 2013/123030 A2 | 8/2013 |
| WO | 2015/013244 A1 | 1/2015 |

OTHER PUBLICATIONS

Written Opinion of the International Searching Authority on the corresponding International Patent Application No. PCT/EP2018/070633, dated Feb. 4, 2020.
Bd Vacutainer, "Helping all people live healthy lives", Jan. 1, 2006 (Jan. 1, 2006), XP055405080, https://iti.stanford.edu/content/dam/sm/iti/documents/himc/immunoassays/BDVacuta inerTubeGuide.pdf.
Bd Diagnostics et al, "Product Catalogue", Jan. 1, 2014 (Jan. 1, 2014), XP055405100, http://www.bd.com/resource.aspx?idx=30 770.
Umetani, Naoyuki, et al. "Increased Integrity of Free Circulating DNA in Sera of Patients with Colorectal or Periampullary Cancer: Direct Quantitative PCR for ALU Repeats." Clinical Chemistry, vol. 52, No. 6, 2006, pp. 1062-1069., doi:10.1373/clinchem.2006.068577.
Vasilakis, Stylianos, International Search Report for PCT/EP2018/070633, dated Sep. 13, 2019.
Toro et al., "Comparison of cell stabilizing blood collection tubes for circulating plasma tumor DNA", Clinical Biochemistry, 2015, pp. 993-998, vol. 48, Elsevier Inc.
Wong et al., "Optimizing blood collection, transport and storage conditions for cell free DNA increases access to prenatal testing", Clinical Biochemistry, 2013, pp. 1099-1104, vol. 46, Elsevier Inc.
Saminathan et al., "Polyamine structural effects on the induction and stabilization of liquid crystalline DNA: potential applications to DNA packaging, gene therapy and polyamine therapeutics", Nucleic Acids Research, 2002, pp. 3722-3731, vol. 30, No. 17, Oxford University Press.

* cited by examiner

*Primary Examiner* — Kenneth R Horlick
(74) *Attorney, Agent, or Firm* — Greer, Burns & Crain, Ltd.; Steven P. Fallon

(57) ABSTRACT

A method for stabilizing cell-free nucleic acids. The method includes providing a composition and applying the composition to a biological sample as a stabilizing agent for the cell-free nucleic acids contained in the biological sample. The composition includes at least one buffering compound that buffers to a pH value of 7 or below, at least one anticoagulant and urotropin in aqueous solution.

17 Claims, 1 Drawing Sheet

Figure 1:
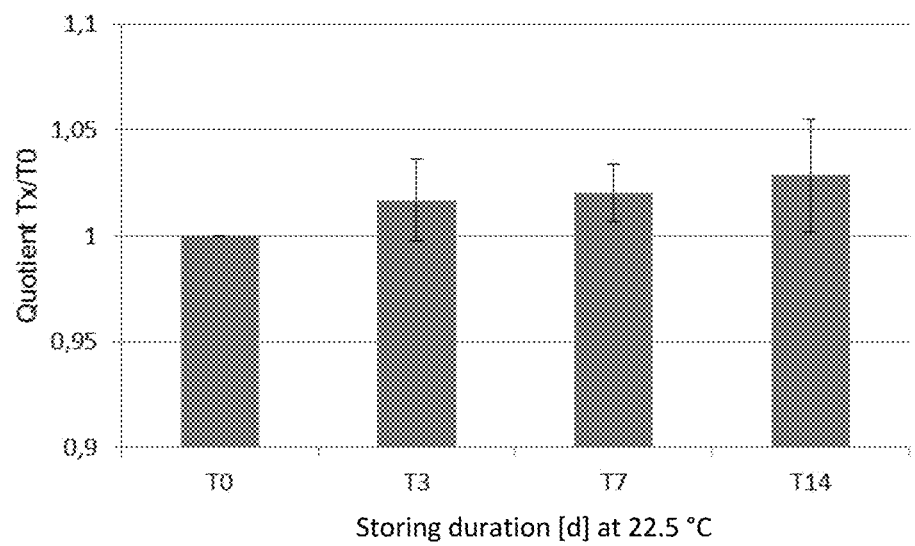

PROCESS AND COMPOSITION FOR THE STABILIZATION OF CELL-FREE NUCLEIC ACIDS AND CELLS

The present invention relates to a process and to a composition for the stabilization of cell-free nucleic acids, in particular of cell-free DNA and/or RNA, as well as alternatively or additionally for the stabilization of cells from biological samples, in particular whole blood or plasma or urine, as well as the use of the composition as a stabilizing agent for cell-free nucleic acids and/or for cells within a biological sample. The composition may be admixed into a cell-free sample or into a cell-containing sample, e.g. by way of a blood collection tube into which whole blood was drawn directly and within which the composition is pre-placed, e.g. pre-placed in an amount equal to 20% of the maximum volume of blood for which the blood collection tube is configured. For urine as biological sample, the composition may be pre-placed in a sample container or may be mixed into the sample filled into the sample container, wherein in each case it is preferred to pre-place the composition in a predetermined volume ratio for a predetermined sample volume or to admix the composition in a predetermined volume ratio to the sample.

The process and the composition have the advantage of stabilizing cell-free nucleic acids contained in the biological sample, particularly for the further analysis, e.g. by means of hybridization, sequencing or amplification, optionally including prior isolation, e.g. by means of adsorption to an adsorption agent for nucleic acids and subsequent elution. The stabilization of cell-free nucleic acids is in particular the preservation of amount and structure of the cell-free nucleic acids, which preservation may also be designated as their integrity.

The composition and the process preferably also have the effect of stabilizing cells contained within the sample, e.g. against a spontaneous lysis, so that on one hand in the collected sample, the nucleic acids contained inside cells are not released or are released in a reduced amount and do not mix with cell-free nucleic acids of the sample, and on the other hand cells may be separated from the sample to allow to analyze cells essentially without impairment from lysis and e.g. free from cell-free nucleic acids. Therein, cells may be those of the sample donor, so endogenous cells, e.g. epithelial cells and/or tumor cells, and cells may be exogenous cells, e.g. bacteria, fungi or yeasts or viruses.

The analysis of cells that are separated from a mixture of the composition with a biological sample may comprise the analysis of intracellular and/or surface-bound proteins, e.g. by immunological analyses. The composition preferably leads to a stabilization of surface-bound proteins on cells.

STATE OF THE ART

WO 2013/123030 A2 describes the admixing of a formaldehyde-releasing compound, especially of diazolidinyl urea or of imidazolidinyl urea in combination with a quencher for the removal of free formaldehyde, e.g. of amino acids, particularly glycine, alkyl amines, polyamines, each in conjunction with EDTA as an anti-coagulant, for the stabilization of whole blood for later analysis of cell-free DNA.

Umetani et al., Clinical Chemistry 52:6, 1062-1069 (2006) describes analysis of the stability of cell-free DNA in serum by means of quantitative PCR amplification of two segments from ALU repeat sequences, one of which segments of 115 bp (ALU115) is located within the other segment of 247 bp (ALU247). The ratio of the amounts of the amplificates forms a measure of DNA quality.

A quotient of 1 of PCR amplificates of ALU247/ALU115, thus equal amounts ALU247 and ALU115, is viewed as characteristic for gDNA, as such a sample contains also the longer templates in addition to the small templates. For cell-free (cf) DNA, Hao, T. B., Shi, W., Shen, X. J., Qi, J., Wu, X. H., Wu, Y., Tang, Y. Y., Ju, S. Q. "Circulating cell-free DNA in Serum as a biomarker for diagnosis and prognostic prediction of colorectal cancer", British Journal of Cancer 111, 1482-1489 (2014) give a quotient of circa 0.3.

WO 2013/045458 for the stabilization of whole blood describes a mixture of dihydroxyacetone as hypertonic additive, N,N-dimethylformamide, N,N-diethylformamide, N,N-dimethylacetamide or N,N-diethylacetamide as a stabilizing agent for extracellular nucleic acids, preferably a chelating agent as an anti-coagulant and an inhibitor of apoptosis that in particular is a caspase inhibitor.

WO 2007/073397 A1 describes a pharmaceutical composition for the treatment of bladder diseases comprising an anionic polysaccharide and an anesthetic drug in buffer, which composition may contain methenamine (equivalent to urotropin) as an antibacterial agent.

OBJECT OF THE INVENTION

The invention has the object of providing an alternative composition and an alternative process for the stabilization of cell-free nucleic acids, e.g. DNA, or of cells in biological samples, particularly in whole blood or urine, for the later analysis, wherein the composition is preferably storage-stable and further preferably has a lower number of different ingredients than known remedies.

DESCRIPTION OF THE INVENTION

The invention achieves the object by the features of the claims and in particular by a composition for use as a stabilizing agent and a process for the stabilization of biological samples, in particular whole blood or urine, in particular for the stabilization of the content and of the integrity of cell-free nucleic acids and/or for the stabilization of the content and of the integrity of cells. The composition comprises or consists of at least one buffering compound in aqueous solution that buffers to a pH value of 7 or below, preferably 3.5 to 7.0, and that is in particular configured to buffer the mixture of the composition and the biological sample to this pH value at least one anticoagulant and/or at least one chelating agent, in particular at least one chelating agent for bivalent cations, preferably for calcium ions, and urotropin, optionally PEG, in particular for use as a stabilizing agent for whole blood. Because chelating agents, in particular EDTA, are also anticoagulants, anticoagulants may be formed by chelating agents for the purposes of the invention. For tuse as a stabilizing agent for urine as biological sample, the composition may comprise the buffering compound and urotropin as a dry mixture, e.g. in powder form, or preferably in aqueous solution, optionally having at least one anticoagulant and/or chelating agent, or consist thereof. Generally preferably, a biological sample is a tissue sample or a body fluid sample of an animal or of a human.

The at least one buffering compound may be selected from citrate buffer, acetate buffer, MES (2-(N-morpholino) ethanesulfonic acid), PIPES (piperazine-N,N'-bis(2-ethanesulfonic acid)), MOPS (3-(N-morpholino)propanesulfonic acid), phosphate buffer and mixtures of at least two of these, or consist thereof. The at least one anticoagulant may e.g. be hirudin, optionally in mixture with a chelating agent. Preferably, the anticoagulant is a chelating agent that may e.g. be selected from citrate and EDTA and mixtures thereof, or may consist thereof.

The composition may be without an added compound as quencher for formaldehyde that is free or dissolved in water, may in particular be without glycine, and/or without an added chelating agent, in particular without EDTA (ethylenediamine tetraacetate), e.g. when the composition contains citrate. Particularly preferably, the composition consists of a solution of citrate buffer and urotropin in water. For the use as a stabilizing agent for cell-free nucleic acids and/or for cells in urine, or respectively in a process for the stabilization of cell-free nucleic acids and/or of cells in urine, the composition may consist of citrate buffer and urotropin, optionally with an anticoagulant and/or chelating agent, in dry mixture in which the citrate buffer is configured to buffer in the sample to a pH value of 7 or below, preferably to 3.5 to 7.0, particularly for a pre-determined sample volume.

The buffering compound preferably has a buffering capacity of a citrate buffer solution that has a concentration in the range of 0.3 to 1 M, preferably 0.4 to 0.7 M, for example 0.5 M, and preferably has a pH value in the range of 3.5 to 7, preferably 4 to 6.5, for whole blood as sample e.g. pH 4 to 4.5, generally more preferably a pH value of 4.5 or 4.2, and is e.g. configured to buffer the mixture of the biological sample and the composition to this pH value. The content of urotropin (hexamethylenetetramine) in the buffer solution preferably is in the range of 1 to 30 wt./vol.-%, preferably 2 or 5 to 25 wt./vol.-%, or up to 20 wt./vol.-%, e.g. 5 to 19 or up to 8 wt./vol.-%. Preferably, the buffering compound is citrate buffer of a concentration in the range of 0.3 to 1 M, more preferably 0.4 to 0.7 M, e.g. 0.5 M, and has a pH value in the range of 3.5 to 7, preferably pH 4 to 6.0, for whole blood as sample e.g. pH 4 to 4.5, generally more preferably a pH value of 4.5 or 4.2, and is preferably configured to buffer the mixture of the biological sample and the composition to this pH value.

It has shown that the citrate buffer sufficiently inhibits the coagulation of whole blood even without containing EDTA. Hence, the at least one buffering compound and the at least one chelating agent may be formed of citrate buffer.

Preferably, in particular for whole blood as biological sample, the composition according to the invention is generated by preparing the buffer that is preferably citrate buffer in water, adjusting the pH value and subsequently adding and dissolving the urotropin. Preferably, the buffer is produced by mixing a solution of the buffering compound, which is e.g. citric acid or acetic acid, in water, with a solution of a salt of the buffering compound, e.g. trisodium citrate or sodium acetate in water, in the respective desired concentration of the buffer, e.g. citrate buffer or acetate buffer. Alternatively, the acid and the salt of the acid are dryly mixed in a ratio, so that the desired pH value is adjusted upon adding liquid.

The composition according to the invention is suitable for use as a stabilizing agent for biological samples, in particular whole blood or urine, in particular for cell-free nucleic acid, DNA and/or RNA, contained in a biological sample, with the subsequent isolation of a cell-free fraction, e.g. of cell-free plasma, or of cells. From the cell-free fraction, in particular cell-free nucleic acids may be analyzed. Therein it has shown that the composition is suitable to stabilize the amount and the structure of cell-free nucleic acids, in particular of cell-free DNA or cell-free RNA in biological samples, in particular whole blood, and to essentially prevent changes of the amount or of the structure of these nucleic acids, so that by the composition essentially no changes are caused in the amount or structure of these nucleic acids that would impair later analysis of the nucleic acids. A later analysis of the nucleic acids may ensue for example by hybridization, sequencing or amplification, e.g. PCR.

The optional content of PEG, e.g. one or a mixture of PEG 6000 to PEG 20000, acts against a hemolysis. Particularly for use for later analysis of cell-free nucleic acid, preferably including isolation of nucleic acids by adsorption to an adsorption agent for nucleic acids, the composition does not contain PEG.

The cells of a biological sample that was mixed with the composition according to the invention are characterized in that their content of nucleic acids, in particular of DNA and RNA, essentially remains unchanged and does not influence the content of nucleic acids of the cell-free fraction.

The composition according to the invention has the advantage that it is storage-stable, e.g. for at least one month, more preferably for at least two months, e.g. for up to eight months or up to six months at 0 to 30° C., more preferably at 5 to 20° C., to achieve the stabilizing effect. Furthermore, the composition is storage-stable even when it is contained in a blood collection tube and is pre-placed therein for the blood to be drawn in, or respectively when it is contained in a urine sample container and is pre-placed therein for urine to be filled in. Accordingly, the invention also relates to a blood collection tube and to the use thereof for the stabilization of cell-free nucleic acids and/or of the cells of a biological sample that is a whole blood sample, wherein the composition is contained in the blood collection tube. Accordingly, the invention also regards a urine sample container and its use for the stabilization of cell-free nucleic acids and/or of the cells of a biological sample that is a urine sample, wherein the composition is contained in the urine sample container.

It has shown that the composition is suitable for the stabilization of nucleic acids and/or of cells without a content of a quencher compound for formaldehyde that is free or dissolved in water, and without an additional content of an anticoagulant like, e.g. EDTA. Presently, the storage stability of the composition and its stabilizing effect on biological samples are attributed to the urotropin in the composition and in the mixture with the sample being present in equilibrium with free formaldehyde, the concentration of which is sufficient for the stabilization and inactivation of proteins, respectively.

Preferably, the composition is contained in a blood collection tube, e.g. in a volume fraction of at maximum 20%, at least 2%, preferably 5 to 15%, particularly 8 to 12%, e.g. equal to 10% of the volume of whole blood which can be drawn into the blood collection tube or for which at maximum the blood collection tube is configured. Preferably, the composition is contained in a urine sample container, e.g. in a volume fraction of at maximum 20%, at least 2%, preferably 5 to 15%, particularly 8 to 12%, e.g. equal to 10% of the volume of urine which can be filled into the urine sample container or for which at maximum the urine sample container is configured.

The process for the stabilization of a biological sample that in particular is whole blood comprises the steps of
contacting the sample with the composition to generate a mixture of the sample and of the composition, preferably in a volume ratio of at maximum 20%, preferably 5 to 15%, particularly 8 to 12% of the composition, which is preferably in aqueous solution, to the sample, optionally storing the mixture of sample and of the composition above 0° C., e.g. at 0 to 37° C., e.g. at 0 to 30° C., more preferably at 5 to 20° C. or at 22.5° C., e.g. for 1 h to 14 d, preferably 5 h to 5 d or up to 3 d or up to 2 d, optionally subsequently separating the mixture into a cell-containing fraction and a cell-free fraction, preferably adding proteinase, e.g. proteinase K, to the generated cell-free fraction following the separation of the mixture, and analyzing the nucleic acids of the mixture from the cell-free fraction thereof and/or analyzing the cells from the cell-containing fraction.

The process for stabilization and analysis of cell-free nucleic acids of a biological sample comprises e.g. the steps of contacting the sample with the composition for the use as a stabilizing agent for the cell-free nucleic acid contained in the sample to generate a mixture of the sample and of the composition, and of storing the mixture of the sample and of the composition at 0 to 30° C. for at least 1 h to 14 d, preferably with subsequent separation of the mixture into a cell-containing fraction and a cell-free fraction, preferably of adding proteinase, e.g. proteinase K, to the generated cell-free fraction after separation of the mixture, and of analyzing the nucleic acids of the mixture from the cell-free fraction thereof and/or of analyzing the cells from the cell-containing fraction, or the process consists of these steps.

Analyzing the mixture optionally comprises isolating nucleic acids, preferably by contacting with an adsorption agent for nucleic acids and subsequent washing of the adsorption agent and eluting bound nucleic acids from the adsorption agent. Applicable adsorption agents, e.g. ion exchange compounds, are e.g. contained in DNA isolation kits by Macherey-Nagel (NucleoSnap DNA Plasma) or Qiagen (QIAamp Circulating Nucleic Acid Kit).

The separation of the mixture into a cell-containing fraction and a cell-free fraction may generally ensue e.g. through filtration or centrifugation and/or through adsorption.

Generally, particularly for urine as a sample, the process, in particular for the cell-free fraction, may comprise at least one step for enrichment of free nucleic acids, e.g. the precipitation of nucleic acids and/or the adsorption of nucleic acids to an adsorbent, e.g. to paramagnetic particles coated with an adsorption agent.

Analyzing the cell-containing fraction may optionally comprise the enrichment of cells from the cell-containing fraction, e.g. the adsorption of cells to an adsorbent, e.g. to paramagnetic particles coated with an adsorption agent, e.g. an antibody.

Optionally, a cell-containing fraction from which the cell-free fraction of a mixture of a biological sample and the composition was separated may be resuspended and solubilized within an aqueous composition such as presently described as stabilizing agent.

Figure 2:
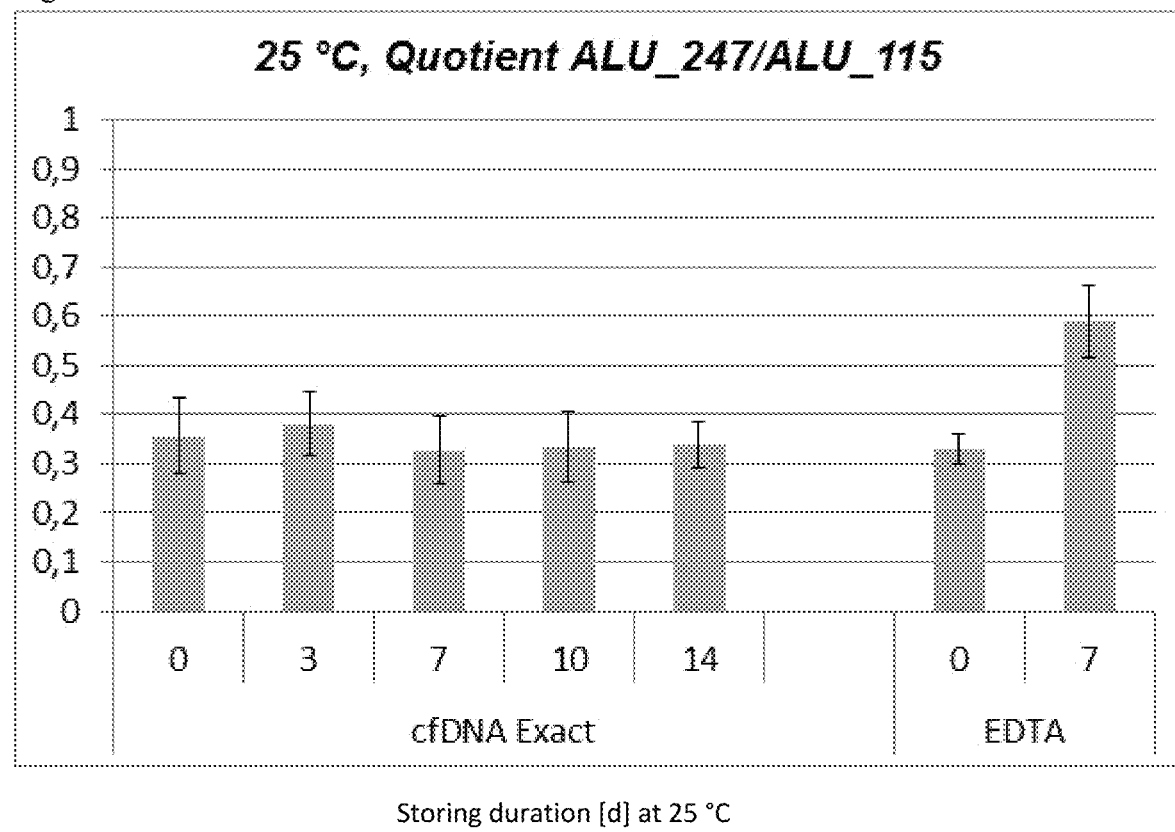

The invention is now described in more detail by way of an example with reference to the figures, which show in FIG. 1 the result of a PCR amplification of cell-free DNA from a sample following different storage periods and in FIG. 2 the result of PCR amplifications of two DNA segments as a quotient of the concentrations of the amplificates following different storage periods.

Example 1: Isolating and Analysing Cell-Free DNA from Whole Blood

The composition was produced by mixing 0.5 M citric acid (monohydrate) in water and 0.5 M trisodium citrate (dihydrate) in water until pH 4.2 was reached and subsequently adding and dissolving of 18 wt./vol.-% urotropin.

As an example for a biological sample, whole blood from 3 donors was drawn into 4 identical blood collection tubes to 4.9 mL each that each contained 0.49 mL of the composition (10 vol.-% of the whole blood). From these blood collection tubes that contained the mixture of whole blood and of the composition and that were stored at 22.5° C., one each was processed on day 0 (T0), day 3 (T3), day 7 (T7) and day 14 (T14), respectively, and cell-free DNA was isolated therefrom and analyzed. For this, a cell-free fraction was generated from each blood collection tube via a two-step centrifugation process (10 min, 2,000×g; 15 min, 15,000×g).

From the cell-free plasma generated thereby that contained the composition for stabilization, cell-free DNA was isolated using the NucleoSnap DNA Plasma Kit (available from Macherey-Nagel). In contrast to the Kit instruction, 1.7 mL of the cell-free plasma instead of 3.0 mL were used, and the lysis buffer VL and ethanol were reduced from 3.0 mL to 1.7 mL accordingly. Additionally, the incubation time for the cell-free plasma with proteinase K at room temperature and at 56° C. was each increased from 5 min to 15 min.

The analysis of the cell-free DNA was done by amplifying the 115 bp segment ALU115 and the 247 bp segment ALU247 by means of quantitative PCR as described by Umetani et al. (2006).

FIG. 1 shows the average of the quotients of the concentration of ALU115 at the given timepoint at day 0 (T0), day 3 (T3=Tx), day 7 (T7=Tx) and day 14 (T14=Tx) of the aliquots and the concentration of ALU115 at day 0 (T0). Therein, a quotient (Tx/T0) of 1 showed that the concentration of cell-free DNA in the mixture stays unchanged respectively stable, and also shows that the cell-free DNA in the mixture is amplifiable through PCR without change. This result shows that the cell-free DNA in the mixture of whole blood and of the composition is stabilized in concentration and structure over a storage duration of at least 14 d at 22.5° C. for the subsequent analysis.

FIG. 2 shows the quotients of the absolute amounts of cell-free DNA (cfDNA) on the example of ALU247 and ALU115 at the given timepoints of storing at 25° C. (day 0 (0), day 3 (3), day 7 (7), day 10 (10) and day 14 (14) for the composition according to the invention (cfDNA Exact) and for EDTA samples (EDTA) on day 0 (0) and day 7 (7)). The result shows the stabilization by the composition according to the invention (Exact) by means of the quotient remaining constant over the incubation time. In non-stabilized, EDTA-anticoagulated samples, the ALU247/ALU115 quotient increases with increasing storage duration. An insufficient stabilization of blood samples/biological samples leads to the lysis of cells and thus to the release of the genomic DNA (gDNA). An ALU247/ALU115 quotient of 1, meaning equal amounts of ALU247 and ALU115, is characteristic for gDNA.

These results also show that the composition is suitable for the later isolation of cell-free nucleic acids from a cell-free mixture of the composition with plasma with adsorbing of the nucleic acids to an adsorption agent, and respectively does not impair this isolation.

Example 2: Isolating and Analysing Cells from Whole Blood

According to Example 1, a mixture of the composition and of whole blood was produced and stored at 22.5° C. A second whole blood sample instead of the composition contained physiological saline solution and EDTA (1.6 mg per mL blood) to prevent coagulation. Out of both kinds of whole blood sample, 5.0 mL each underwent an erythrocyte lysis on day 0, day 1, day 3 and day 5, respectively, and the circulating endothelial cells (cEC) were enriched and analyzed by means of the cEC Enrichment and Enumeration Kit of the company Miltenyi Biotech. In healthy humans, the number of circulating endothelial cells lies at ca. 1-20 cells per mL. In various diseases, the number of cECs is in some cases substantially increased. Stabilizing compounds have to ensure that the number of cEC in stored blood samples is stable. Following the analysis described for the Kit, it has shown that over the storage duration the number of evidenced cEC stayed constant only in the samples stabilized according to the invention.

Example 3: Isolating and Analysing Cell-Free DNA from Urine

The composition was produced by mixing 0.5 M citric acid (monohydrate) in water and 0.5 M trisodium citrate (dihydrate) in water until pH 4.2 was reached and subsequently adding and dissolving 15 wt.-%/vol.-% urotropin.

As an example for a biological sample, 90 mL urine were mixed with 1/10 vol. of the composition immediately after sampling. From this mixture that was stored at 22.5° C., one aliquot was each processed on day 0, day 3, day 7 and day 14 and from this cell-free DNA was extracted and analyzed. For this, one cell-free fraction each was generated through centrifugation at 15,000×g for 15 min and separation of the cell-free fraction from one aliquot. From the thus generated cell-free fraction that contained the composition for stabilization, cell-free DNA was isolated by means of the Nucleo-Snap Plasma Kit (available from Macherey-Nagel).

Compared to urine samples that were identically stored without treatment or with addition of an equal volume of physiological saline solution or of dissolved buffering compound only, it has shown that cell-free DNA was stabilized by the composition.

Example 4: Analysing Stabilized Cells in Urine

According to Example 3, urine was mixed with prostate carcinoma cells (LnCap) and was mixed and stored with the composition or, for comparison, with physiological saline solution.

The analysis ensued on cells sedimented through centrifugation after identical storage period of the comparative samples. It showed that only the composition according to the invention allowed for the flow cytometric detection of the added cells.

Compared to urine samples that were identically stored without treatment or with addition of an equal volume of physiological saline solution or of dissolved buffering compound only, it has shown that the composition stabilized surface markers of the cells during storage.

The invention claimed is:

1. A method for stabilizing cell-free nucleic acids, the method comprising providing a composition and applying the composition to a biological sample as a stabilizing agent for the cell-free nucleic acids contained in the biological sample, wherein the composition comprises at least one buffering compound that buffers to a pH value of 7 or below, at least one anticoagulant and urotropin in aqueous solution.

2. The method according to claim 1, wherein the composition consists of the at least one buffering compound, the at least one anticoagulant which is a chelating agent, and the urotropin.

3. A method for stabilizing cell-free nucleic acids, the method comprising providing a composition and applying the composition to a biological sample as a stabilizing agent for the cell-free nucleic acids contained within the biological sample, wherein the composition comprises, as a dry mixture, at least one buffering compound that is configured to buffer the biological sample to a pH value of 7 or below, at least one anticoagulant and urotropine.

4. The method according to claim 1, wherein the composition contains no quenching compound for free or for dissolved formaldehyde.

5. The method according to claim 1, wherein the at least one buffering compound buffers the aqueous solution to a pH value in the range of 3.5 to 7 and has a buffer capacity that is equal to a concentration of 0.3 to 1 M citrate, and in that 1 to 30 wt./vol.-% urotropin is dissolved in the solution.

6. The method according to claim 1, wherein the at least one buffering compound and the at least one anticoagulant are formed by citrate buffer.

7. The method according to claim 1, wherein the at least one buffering compound is selected from citrate buffer, acetate buffer, MES (2-N-morpholinoethanolsulfonic acid), PIPES (piperazine-N,N'-bis-2-ethanolsulfonic acid), MOPS (3-N-morpholinopropanesulfonic acid), phosphate buffer and mixtures of at least two thereof, and in that the at least one anticoagulant is a chelating agent selected from citrate and EDTA and mixtures thereof.

8. The method according to claim 1, wherein the biological sample is whole blood and the composition is contained in a blood collection tube in a volume fraction of up to 20% of the maximum sample volume to be drawn, for which the blood collection tube is configured.

9. The method according to claim 1, wherein the biological sample is urine.

10. The method according to claim 1, wherein the biological sample in a mixture with the composition is stable at 0 to 37° C. for 1 h to 14 d.

11. The method according to claim 1, wherein the applying comprises
contacting the sample with the composition to produce a mixture of the biological sample and the composition and
storing the mixture of the biological sample and the composition at 0 to 37° C. for 1 hour to 14 days.

12. The method according to claim 11, wherein the composition is contacted with the sample in a volume fraction of at maximum 20% of the sample volume.

13. The method according to claim 11, comprising, separating the mixture into a cell-free fraction, and adding proteinase to the mixture prior to the storing.

14. The method according to claim 13, comprising isolating nucleic acids from the cell-free fraction and analyzing the cell-free fraction.

15. The method according to claim 1, wherein the biological sample is whole blood or urine.

16. The method according to claim 1, wherein the anticoagulant is a chelating agent and the composition comprises PEG.

17. The method according to claim 3, wherein the anticoagulant is a chelating agent and the composition comprises PEG.

\* \* \* \* \*